US010799713B2

(12) United States Patent
Bean et al.

(10) Patent No.: US 10,799,713 B2
(45) Date of Patent: Oct. 13, 2020

(54) MINIATURE WEARABLE LASER TREATMENT DEVICE

(71) Applicant: Veralase, LLC, Danvers, MA (US)

(72) Inventors: David Bean, Middleton, MA (US); Zilong Huang, Malden, MA (US); Shalini Sreedhar, Weston, MA (US)

(73) Assignee: Veralase, LLC, Peabody, MA (US)

(*) Notice: Subject to any disclaimer, the term of this patent is extended or adjusted under 35 U.S.C. 154(b) by 94 days.

(21) Appl. No.: 16/103,279

(22) Filed: Aug. 14, 2018

(65) Prior Publication Data

US 2019/0046811 A1 Feb. 14, 2019

Related U.S. Application Data

(60) Provisional application No. 62/545,013, filed on Aug. 14, 2017.

(51) Int. Cl.
*A61N 5/06* (2006.01)
*A61K 39/00* (2006.01)
*A61K 39/39* (2006.01)
*A61N 5/067* (2006.01)

(52) U.S. Cl.
CPC .............. *A61N 5/062* (2013.01); *A61K 39/00* (2013.01); *A61K 39/39* (2013.01); *A61N 5/0616* (2013.01); *A61N 5/0622* (2013.01); *A61K 2039/54* (2013.01); *A61K 2039/55588* (2013.01); *A61N 2005/067* (2013.01); *A61N 2005/0645* (2013.01)

(58) Field of Classification Search
CPC ............. A61N 1/36053; A61N 1/0456; G01N 33/6863

USPC ........................................................ 607/116
See application file for complete search history.

(56) References Cited

U.S. PATENT DOCUMENTS

| 8,246,667 B2 | 8/2012 | Cornil et al. |
| 8,888,830 B2 | 11/2014 | Dunleavy et al. |
| 9,333,371 B2 | 5/2016 | Bean et al. |
| 9,370,449 B2 | 6/2016 | Anderson et al. |
| 2010/0063489 A1 | 3/2010 | Cornil et al. |
| 2014/0121631 A1 | 5/2014 | Bean et al. |
| 2014/0276358 A1 | 9/2014 | Kashiwagi et al. |

(Continued)

FOREIGN PATENT DOCUMENTS

| WO | 02100484 | 12/2002 |
| WO | 2009111010 | 9/2009 |

OTHER PUBLICATIONS

Kimizuka, Y. et al. "Semiconductor diode laser device adjuvanting intradermal vaccine". Vaccine, Apr. 25, 2017, vol. 35 issue 18, 2404-2412.

(Continued)

*Primary Examiner* — Nadia A Mahmood
(74) *Attorney, Agent, or Firm* — Onello & Mello LLP

(57) ABSTRACT

A portable, miniature laser device that is capable of accurate bodily placement and registration of treatment area for extended timeframes which is useful in long-duration treatments and multi-step treatments of tissue where accurate tissue registration is required, such as treatments requiring vaccine shots or other medications provided to tissue after laser irradiation. Example applications include: improving vaccine efficacy, reducing warts, skin rashes, skin cancer, fungal diseases and promoting wound healing.

19 Claims, 13 Drawing Sheets

(56) References Cited

U.S. PATENT DOCUMENTS

2015/0238774 A1* 8/2015 Anderson ............ A61K 35/04
                                                    604/20
2016/0038763 A1   2/2016 Tapper et al.

OTHER PUBLICATIONS

International Search Report and Written Opinion dated Jan. 16, 2019 issued in corresponding International Application No. PCT/US2018/046664.

* cited by examiner

MINIATURE WEARABLE LASER TREATMENT DEVICE

RELATED APPLICATIONS

This application claims the benefit of U.S. Provisional Patent Application No. 62/545,013 filed on Aug. 14, 2017, the content of each of which is incorporated herein by reference in its entirety.

BACKGROUND OF THE INVENTION

Lasers are commonly used in cosmetic, medical, and surgical applications. In the cosmetic industry, laser uses include hair removal, acne reduction, wart removal, and wrinkle reduction. Medical professionals use laser technology commonly in surgery to cut, coagulate, and cauterize tissue. Lasers are also often used in medicine to treat skin-based ailments including: warts, rashes, skin cancer, fungal diseases and wounds. These lasers are large, expensive, complicated to operate, and require personnel specifically trained in medical laser usage.

Researchers in medical science are finding ways to use laser light to stimulate the human cellular structure to condition certain tissues such that there is an improved immune response. In some cases, lasers are used to increase the immune response in a way that improves how well a vaccine is taken-up by the body's immune system. In this case, the laser is considered a vaccine adjuvant, as it improves the human response to the given vaccine. In other cases, lasers are used to dampen an immune response so that the human response to a stimulus is muted. This is useful, for example, when a person is highly allergic to a substance and such a laser treatment can reduce or eliminate the overreactive immune response.

Most conventional vaccine adjuvants are, however, chemical compounds that are combined with the vaccine solution to enhance the immune response to the vaccine. Typically, these chemical adjuvants cause discomfort where the vaccine is injected in the body and/or result in other unwanted side effects. Highly effective adjuvants often result in unacceptable local reactogenicity or systemic toxicity which is unacceptable and unsafe for human use.

SUMMARY OF THE INVENTION

Embodiments of the present inventive concepts include a laser system that has a small footprint, for example, typically no longer than 120 mm, or no wider than 80 mm, or no thicker than 40 mm and no heavier than 5 pounds and preferably less than 20 oz, allowing the laser system to be portable. In preferred embodiments, the laser system is smaller than 120×80×40 mm in size. The laser system may be battery powered, preferentially with Li+ type rechargeable batteries built into the laser system. The laser system may be used for promoting wound healing, as a vaccine adjuvant, or to treat indications such as warts, skin rashes, forms of skin cancer, and fungal infections. The system is capable of peak laser powers of 20 mW or greater and preferentially capable of peak laser output powers of 100 mW or greater.

The system has an operator interface panel on the outside surface with buttons for adjusting power, starting and stopping laser operation, and adjusting laser settings. An optional LCD display or LED indicators can display the laser system status as well as prompt action or provide feedback to the user. The LCD screen may be a touch-enabled screen that can display logical buttons and controls that a user may activate or adjust by touching the screen. The system treatment time is typically longer than 2 seconds and may be up to 60 minutes or longer.

A mounting frame structure may be used to attach the laser system to the person for treatment. The mounting frame preferably comprises an inexpensive material such as plastic, rubber or the like, and may be a disposable consumable used in the treatment process. The mounting frame preferably has an adhesive backing to stick to and mount to the person on one side and has hook and/or snap elements that register into corresponding elements on the outside of the laser system to mount and hold the laser system accurately and consistently in the frame so that the laser treatment is applied to the person in a consistent spot of interest.

The mounting frame preferably has an integrated element that will identify a precise location of laser treatment either before and/or after the laser treatment is completed. One integrated spot element may be a circular ring that folds up when the laser is snapped into the mounting frame, and the integrated spot element hinges down to indicate the treatment spot when the laser system is removed from the mounting frame. This circular ring may be used to line up the treatment spot with the frame prior to attaching the laser system, thereby ensuring the laser system is appropriately aligned to the treatment spot of interest. The circular ring may also be used to fold down after the laser treatment is completed and act as a guide for administering a vaccine shot in the same spot as the laser treatment. In this case, the ring is preferably having an inner diameter that closely matches the outer diameter of the syringe of the vaccine delivery device so that the needle of the vaccine delivery device aligned to the center of the laser treatment area. The integrated spot element may alternatively be of a geometry other than a ring, such as a square or oval, or shape that mates with the vaccine delivery device and preferably centers the vaccine shot to the center of the laser treatment area.

An alternative approach for registering a laser system to a treatment spot of interest is to use a sticker, or a relatively thin piece of paper, vinyl, or similar pliable material, with an adhesive on one side. The sticker is shaped in a form that gives guidance of the outline of the laser system so that the laser operator may hold a laser source of the system in the appropriate place or preferably strap the laser source in the appropriate place for treatment. The sticker also preferably has a geometry that outlines the treatment area of interest, as registered to the laser system when held or mounted correctly to the outline geometry. This sticker outline of the treatment spot can be used to align the sticker to the treatment spot of interest and subsequently align the laser system to this same spot through correct positioning to the sticker outline. The sticker spot outline also provides accurate treatment spot outline for aligning a post-treatment vaccine or drug shot to the center or within the boundaries of the treatment area.

In another approach, an inking system such as a stamp or drawing stencil can be used such that the outline of the treatment area as well as the outline of the laser system relative to the treatment spot or the center position of the treatment spot may be marked. This approach provides a marked area for treatment and for positioning the outline of the laser system so that the laser emissions match the desired treatment spot.

In another approach, a light-sensitive material or solution may be applied to the skin such that it changes color when exposed to laser light. Using this method, the light-sensitive material or solution is applied to the skin, then a laser treatment is performed. When the laser is removed, the color-changed area indicates the area treated by the laser. This indicates to the medical personnel the area for the needed shot or further treatment in new or identical areas.

In the abovementioned approaches, instead of outlines of the laser system for alignment, simple matching fiducials may be used to position the laser to the treatment spot of interest. In this approach, it is preferable that the material(s) applied to the skin for fiducials (that will match similar markings on the laser device) be easily removed and/or washed off the patient after use. If a strap, band, or the like is used to hold the laser system in place, it is preferable to use Velcro-like or elastic material to secure the strap to allow for easy and fast strapping and unstrapping, similar to most common blood-pressure cuffs. The strap, or band or the like, may operate to mount with the frame, sticker, or ink registration with respect to a laser treatment and for positioning about the wearer's arm. In another embodiment, the strap, or band or the like, may operate such that it has an integrated pocket, clip-in feature or fastener system to hold the laser system during treatment, and when the laser system is removed or pivoted away from the strap, or band or the like, there is a clear indication of where the laser radiation on the skin occurs based on the geometry of the exposed skin not covered by the band, such as a circular hole in the band where the light irradiated through, and such geometry acts as a guide for administering a subsequent shot of vaccine or drug solution.

In another approach, the laser system is attached to an easily adjustable and removable attachable strap, for example, a Velcro strap, while the laser treatment takes place. The strap may have an area with a flat circular ring or other geometry with similar geometry as the laser treatment area (no not necessarily the same geometry) and whereby the center of the outlined area corresponds to the center of the laser treatment. The laser system can be removed from the strap after treatment and the disk on the strap will indicate the location where the laser treatment occurred and where further treatment should be administered.

The backing material of the laser system includes preferably a good thermal conductive material such as an aluminum, copper, or steel compound. Using the thermally conductive material on the back of the laser system provides a heatsink for laser system waste heat and allows the undesirable waste heat to exit the laser system into the person being treated, as this surface will be in direct contact with the skin. Since the human body skin external temperature is typically around 31° C. and the air temperature is typically between 20-25° C., the human body will act to slightly warm the laser system and maintain it at a temperature around 30° C. Most laser system wavelengths change to longer wavelengths as temperature increases and shorter wavelengths as temperature decreases. Laser diodes, for example, experience a wavelength drift between 0.3 nm/° C. to 0.7 nm/° C. For example, a 1270 nm laser diode at 30° C. with a temperature shift of 0.6 nm/° C. will shift to 1276 nm at 40° C. By keeping the laser system temperature relatively stable and close to 30° C., the laser wavelength will not drift as much as it otherwise would without this temperature management using the skin as a heatsink.

In some embodiments, a method of using the person's body temperature to stabilize the laser temperature reduces the complexity, size, and cost of the laser system because additional cooling or heating is not required to maintain wavelength stability. Typically, a laser diode system will use a thermoelectric cooler (TEC) to maintain the laser diode temperature, however, this approach adds significant cost, significantly drains the battery power due to the TEC electrical consumption, and still requires an external heatsink to remove the heat from both the laser diode and TEC. Other approaches to maintain wavelength involve using laser chips with relatively fixed wavelength stabilization such as distributed feedback lasers (DFB), distributed feedback reflectors (DBR), or fiber bragg grading feedback (FBG-stabilized). Each of these methods adds costs and often dramatically lowers the output power of the laser diode. It is often adequate to maintain the laser temperature heatsink between 20 and 40° C. using a human skin contact to achieve temperature stability within this range. Contact with the human or skin or tissue proves thermal heat stabilization in this temperature range 20 to 40° C. This approach avoids the complexity, cost and size issues related to DFB, DBR and FBG-stabilized laser designs. As an added element to improve temperature stability, a heater element may be included in the laser system to enable the laser to pre-heat to a temperature at or near 30° C. so that initial laser operation will commence at or about 30° C. operating conditions without having to wait for the skin or laser waste heat to bring the laser into this temperature zone. The added heating element may accelerate the treatment as the system does not need to wait as long for temperature to stabilize, if this is a condition of laser operation.

The laser system may communicate electronically with a docking station or other apparatus for convenient charging. In some embodiments, the docking station has an inner pocket that matches the outside geometry of the lower portion of the laser system and electrical charging contacts inside the pocket that mate with external charging contacts on the laser system when the laser system is fully engaged in the docking station.

Laser diodes are the preferred laser source to be used in the laser system design due to their small size, high efficiency, low cost, and available wavelengths between 220-2000 nm. It is preferable to incorporate a safety sensor into the side of the laser system that contacts the skin and emits the laser light. One method incorporates a capacitive or resistive sensor behind the window element where the light exits the laser system. Another method incorporates an optical sensor to identify contact with the skin.

In one aspect, provided is a system for providing a localized laser treatment to a targeted region of skin or tissue for treating a patient. The system comprises a laser system comprising a surface; and a laser transmission window at the surface from where a source of laser light is output; a removable frame comprising: an adhesive backing that attaches to a region surrounding a targeted region of patient skin or tissue; at least one connecting member for removably, securely, and precisely coupling the laser system to the frame so that the surface including the laser transmission window is positioned at an interior region of the frame, and so that the source of laser light is output through the interior region of the frame to form an irradiation spot at the targeted region of skin or tissue.

In one aspect, a system for providing a localized laser treatment to a targeted region of skin or tissue for treating a patient comprises a laser system comprises: a surface; and a laser transmission window at the surface from where a source of laser light is output; a removable frame, comprising: an adhesive backing that attaches to a region surrounding a targeted region of patient skin or tissue; at least one connecting member for removably, securely, and precisely coupling the laser system to the frame so that the surface including the laser transmission window is positioned at an interior region of the frame, and so that the source of laser light is output through the interior region of the frame to form an irradiation spot at the targeted region of skin or tissue; and a pivotable registration member that, in a first position, is removably coupled to the surface of the laser system, and in a second position, is positioned over the targeted region of skin or tissue.

In another aspect, a system for providing localized laser treatment of a targeted spot of skin or tissue for treating a patient comprises a laser system including a side surface from which laser light is emitted; and a removable sticker having an adhesive backing that attaches to a region surrounding a targeted region of patient skin or tissue, the removable sticker further having an inside edge or printed outline that matches an outside edge of the laser system, wherein when the side surface of the laser system is positioned against the targeted region of skin or tissue, and the outside edge of the laser system is aligned with a sticker outline or printed outline markings, the laser emission area on the skin or tissue has a common center to markings or inner edges of the sticker, wherein the common center provides an accurate indication of where laser light treated the skin or tissue after the laser system is removed.

In another aspect, a system for providing localized laser treatment of a targeted spot of skin or tissue for treating a patient comprises a laser system including a side surface from which laser light is emitted; a marking or inking system including a stamp, stencil, or writing instrument for marking the targeted spot skin or tissue to form an outline that aligns with or matches an outside edge of the laser system or corresponding marking fiducials, wherein when a laser system light emitting surface is held against the targeted spot of skin or tissue and the laser system outside edge is aligned with the skin or tissue markings, the laser emission area on the skin or tissue has a common center to skin or tissue markings, and the common center provides an accurate indication of where laser light treated the skin or tissue after the laser system is removed.

In another aspect, a system for providing localized laser treatment of a targeted spot of skin or tissue for treating a patient comprises a laser system with laser light emitting primarily out one side; a strapping system where the laser system is attached to the strap during treatment and when the system is removed from the strap or pivoted away from the skin while still on the strap, the laser treatment location is indicated by a ring on the strap or other physical geometry opening with a common center to the laser emission area, and such common center provides an accurate indication of where laser light treated the skin or tissue after the laser system is removed.

In another aspect, a method for providing localized laser treatment of a targeted spot of skin or tissue for treating a patient comprises mounting a laser system directly onto a patient's skin; and using person's natural skin or tissue temperature to maintain laser system temperature between 20 to 40° C.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF EMBODIMENTS

Figure 1:
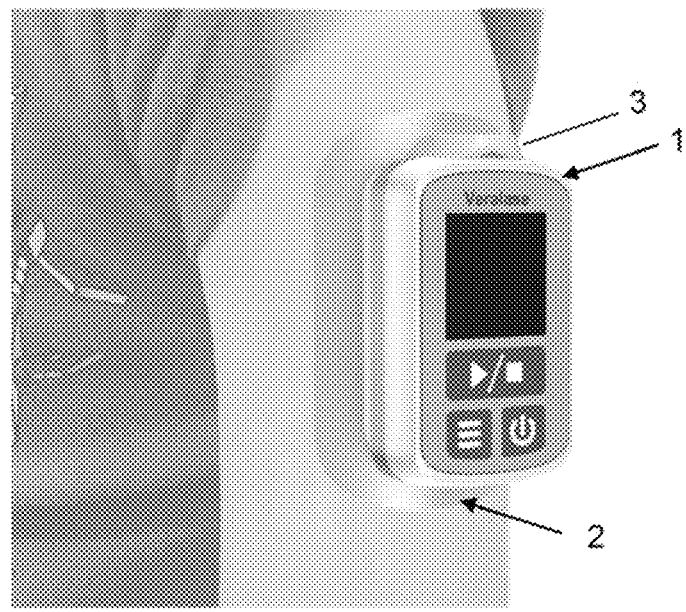
FIG. 1 is a perspective view of a laser system mounted on a person, in accordance with some embodiments.

One embodiment of the present invention includes a laser system that has a small footprint no longer than 120 mm, or no wider than 80 mm, or no thicker than 40 mm or no more than 384 cm$^3$ in volume and no heavier than 5 pounds and capable of peak laser powers of 20 mW or greater. Preferable embodiments specification of the invention include a size of less than 100×60×40 mm in any dimension or no more than 240 cm$^3$ in volume and less than 20 oz in weight, capable of peak laser powers of 100 mW or greater. The laser system is preferably battery operated, preferentially with Li+ type rechargeable batteries built into the laser system. The laser system may be used for promoting wound healing, as a vaccine adjuvant, or to treat indications such as warts, skin rashes, forms of skin cancer, and fungal infections. The laser wavelength shall be between 200 nm and 2000 nm and preferably between 1000 and 1400 nm. An optimal wavelength for certain diseases is between 1200 and 1310 nm, which some embodiments favor, and some further embodiments favor a more narrow wavelength range of 1250 to 1300 nm to optimize treatment efficacy.

Therefore, in some embodiments, using laser light as a vaccine adjuvant instead of chemicals can increase vaccine efficacy without the discomfort and unwanted side effects. Increasing the vaccine efficacy has the benefit of making weak vaccines effective enough for effective use. For example, influenza vaccines to elderly populations are often ineffective and could be made effective using a laser adjuvant prior to administering the vaccine. Many vaccines in development for diseases such as Chikungunya, Zika, Tuberculosis, and Malaria are weak and will not be commercialized without an adjuvant to boost their efficacy. Other vaccines require a series of shots or "boosters" to gain suitable immunity from disease; this is a problem in poor and underdeveloped areas where it is difficult to bring medical supplies and personnel to vaccinate people more than once. These problems of low potency and multiple vaccinations may be resolved with laser adjuvants instead of or in addition to chemical adjuvants.

Investigators at the Vaccine and Immunotherapy Center (VIC), Massachusetts General Hospital (MGH) recently identified a new adjuvant approach with the potential to address this need. MGH found that non-harmful laser treatment of a small area of the skin before intradermal vaccination at certain wavelengths between 1000 to 1300 nm increases both humoral and cell-mediated immune responses to a clinically-relevant vaccine in a mouse model and showed a significant survival advantage in a lethal challenge murine model of influenza, described in U.S. Patent Application Publication No. US 2014/0276358 A1, incorporated by reference herein in its entirety. Results indicate here that laser irradiances and doses equivalent to those used in mice have been shown to be non-painful in humans. Wavelengths near 1061, 1258 and 1301 nm demonstrated vaccine adjuvant efficacy using power levels of less than 2.0, 1.7, and 1.6 watts respectively, and treatment area of 0.25 cm$^2$. The most effective and preferable wavelength was found to be 1258 nm in these experiments. This work builds on previous studies that used visible light, high-frequency, ultrashort duration pulsed lasers to enhance immune responses to intradermal vaccination.

Conventional laser systems for medical applications are large and expensive, in particular, weighing more than 5 pounds, and often more than 100 pounds, and are large self-standing floor units and costing over $30,000. These lasers are large and expensive due to their complexity and choice of technology to achieve the laser output. Typical home-remedy lasers for hair removal and skin treatments weigh one or more pounds and cost $500 or more. In order for lasers to see widespread use as vaccine adjuvants or for general medical use, lasers must be inexpensive, compact, robust, and easy to use. Lasers for vaccines, medical use, or surgical use are preferably be less than 10 oz in weight, less than $4000 in cost, battery-powered, rugged, and be handheld or able to be mounted or strapped directly to the human patient. Home-based lasers desire similar characteristics with retail prices of $400 or less.

There are a number of past and current examples of laser treatments for skin that may apply for both home and medical use. For example, U.S. Pat. No. 8,888,830, incorporated by reference herein in its entirety, describes a laser system and process using a near-IR laser to produce controlled variable heating of the skin without pain. These laser designs and approaches typically have a headpiece where the laser treatment is relatively fast, applied within a few seconds per treatment spot, and repetitive as the treatment moves from spot to spot. However, this approach is not suitable for laser treatment times of 2 seconds or longer during which a source of laser light is directly applied to the treatment area. Handheld lasers and floor or table based units with hand-pieces are not convenient and are less effective for these long treatment cycles.

Treating indications such as warts, skin rashes, forms of skin cancer, and fungal infections often require the laser light to be positioned accurately over the tissue of interest for a significant period of time, longer than 2 seconds and up to 60 minutes. Similarly, for laser adjuvant applications, the laser needs to be both accurately placed and maintained in this accurate position for between 2 seconds and 20 minutes. In addition, the mounting of the laser on the person must be performed so as to register where the vaccine shot should be administered after the laser adjuvant treatment is completed such that the vaccine shot occurs at the center, or near the center, of the laser irradiation spot. Current laser systems do not address the issues of maintaining an accurate placement of a laser adjuvant application for these time periods and registering the spot for follow-on treatment such as vaccine shots.

FIG. 1 illustrates a laser system 1 mounted into a mounting frame 2 and secured by a pivotable registration member, also referred to as a snap ring 3. The mounting frame 2 is preferably affixed to a human below the shoulder where vaccine shots are typically administered, but not limited thereto. Alternate methods may equally apply of placement of the mounting frame 2 and system 1 on any skin area of interest to address the laser treatment spot of interest.

Figure 2:
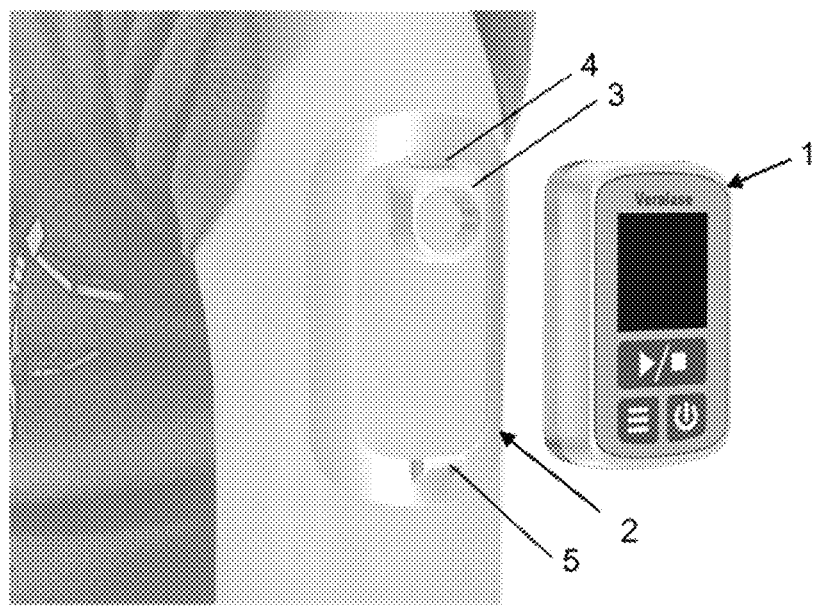
FIG. 2 is the system from FIG. 1 with the laser system unmounted from the frame, in accordance with some embodiments.

FIG. 2 illustrates the laser system 1 of FIG. 1 detached from mounting frame 2 with clip element 5 shown, which supports holding the laser system 1 in place when removably coupled or mounted to the mounting frame 2. The frame 2 includes snap ring 3, which pivots or rotates in the down position, outlining the location of the laser treatment spot. A hinge element 4 extending between the snap ring 3 and the mounting frame 2 is preferably integrated into the mounting frame 2 and automatically springs into a position illustrated in FIG. 2, for example, a down position 90 degrees relative to the mounting position of the snap ring 3 shown in FIG. 1.

Figure 3:
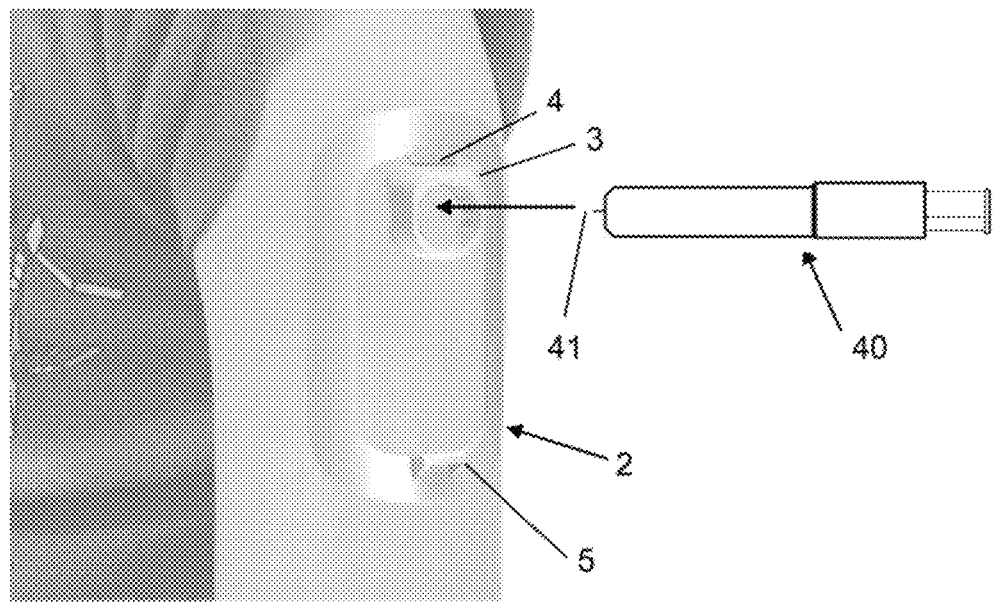
FIG. 3 is a perspective view illustrating the frame of FIGS. 1 and 2 aligning a needle for treatment, in accordance with some embodiments.

FIG. 3 illustrates the mounting frame 2 in communication with a syringe 40 by way of an arrow indicating how the syringe 40 is easily aligned to a laser treatment area using an outline formed or otherwise demarcated by the snap ring 3 when the mounting frame 2 is affixed to desired region of interest where a vaccine or the like is preferably administered from the syringe 40. The syringe needle 41 is preferably necessarily aligned to the center of the laser treatment area. The inside geometry of the snap ring 3 is preferentially the same or similar to the outside geometry of syringe 40 such that syringe 40 mates into snap ring 3 during the shot application causing the needle 41 to be centered to the laser treatment area.

Figure 4:
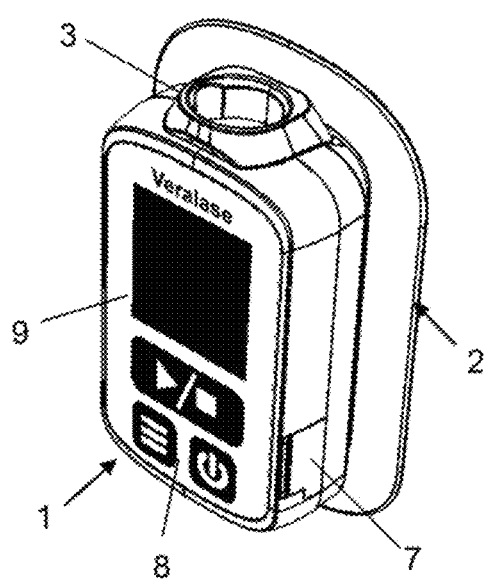
FIG. 4 is a front perspective view of a laser system with a mounting frame, in accordance with some embodiments.

FIG. 4 illustrates an LCD display 9, membrane touchpad 8, with power, menu, and start/stop buttons, port cover 7 of the laser system 1 mounted into mounting frame 2 but not yet mounted onto the person.

Figure 5:
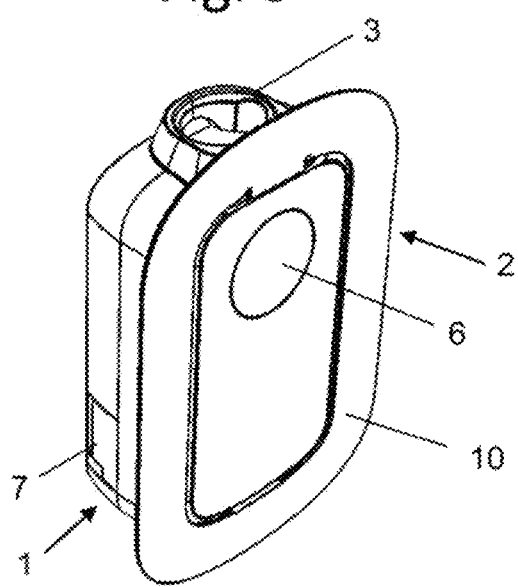
FIG. 5 is a back-side perspective view of the system in FIG. 4.

FIG. 5 is the laser system 1 as in FIG. 1 mounted into mounting frame 2 with a backside perspective showing laser transmission window 6, also referred to as a laser window, and snap ring 3 which is on the same centered-location as the window 6 when laser system is not in mounting frame 2 as shown in FIG. 3. Mounting frame back region 10 has an adhesive coating that may be protected by a wax-like paper prior to use. This back region 10 is used to adhere the frame 2 and connected laser system 1 to the person being treated.

Figure 6:
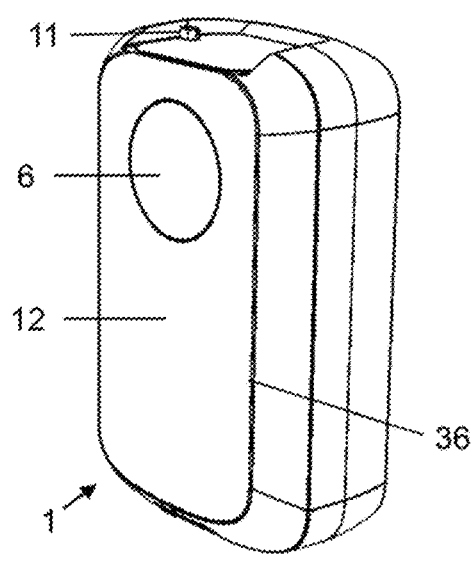
FIG. 6 is a back-side perspective view of the laser system, in accordance with some embodiments.

FIG. 6 illustrates the laser system 1 from a backside perspective, and in particular shows a laser transmission window 6, snap feature 11 and laser back 12. The material for the laser back 12 preferably includes a thermal conductor such as an aluminum, copper, or steel compound for thermal performance. Window 6 is transparent to the wavelength(s) emitted by laser system 1 and preferably made of glass, plastic, or related material.

The inside edge geometry of the mounting frame 2 is preferably matched to the backside edge 36 so that when laser system 1 is snapped into mounting frame 2, there is a snug fit that holds the laser system 1 in a fixed position while allowing the surfaces of the laser back 12 and the mounting frame back region 10 to be on the same plane and have contact with the human skin as shown in FIG. 1. This direct contact between the laser back 12 and the surface of the skin provides good thermal conduction between the laser system 1 and the person being treated. The direct contact also provides intimate contact between the laser window 6 and the skin, which provides safe laser emission from the laser to the skin without allowing stray light into the air and causing an eye-safety or other radiation concern. This intimate window/skin contact may be verified with capacitive or resistive sensors in close proximity to the window and laser emissions area. The adhesion of the mounting frame back region 10 to the skin ensures the laser will stay in the same place during treatment without disruption. Although the laser system 1 is described herein as generating and outputting a source of laser light, the system 1 is not limited to the frequency spectrum of laser light, and other frequencies may equally apply where other sources of electromagnetic radiation may be output. In other words, although laser light is referred to in some embodiments, any region of the electromagnetic spectrum may equally apply to achieve the desired features of the inventive concept.

Figure 21:
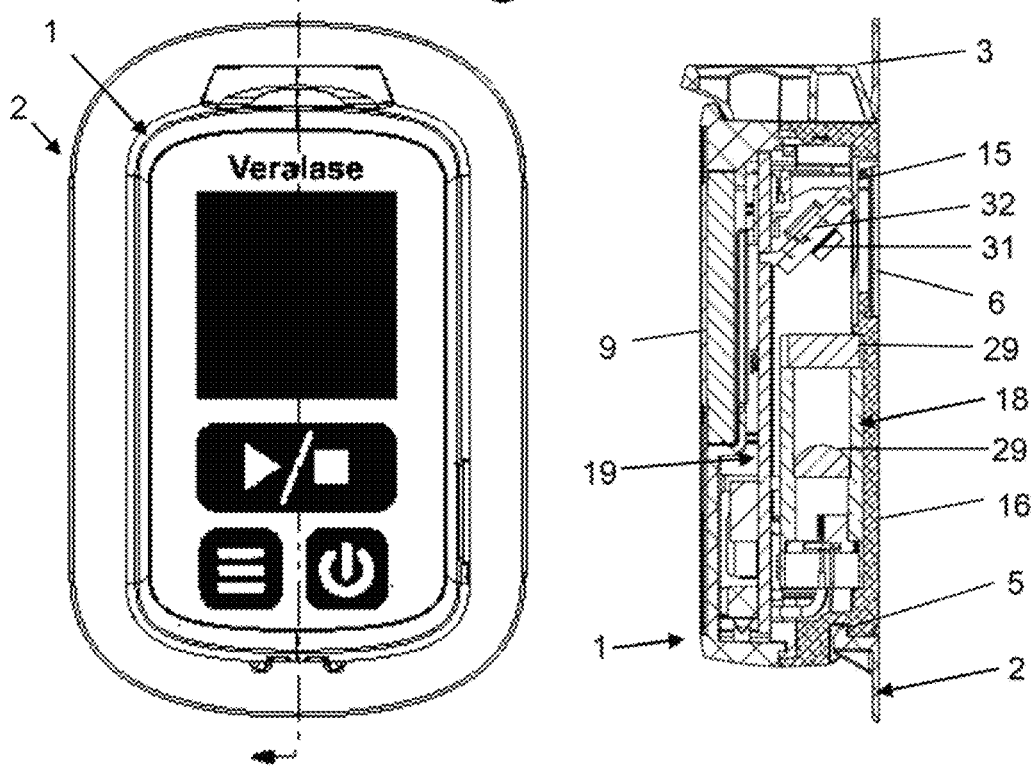
FIG. 21 is a cross-section of FIG. 4 where the cross-section plane is directly through one of the snap feature 11 of FIG. 8.
Figure 22:
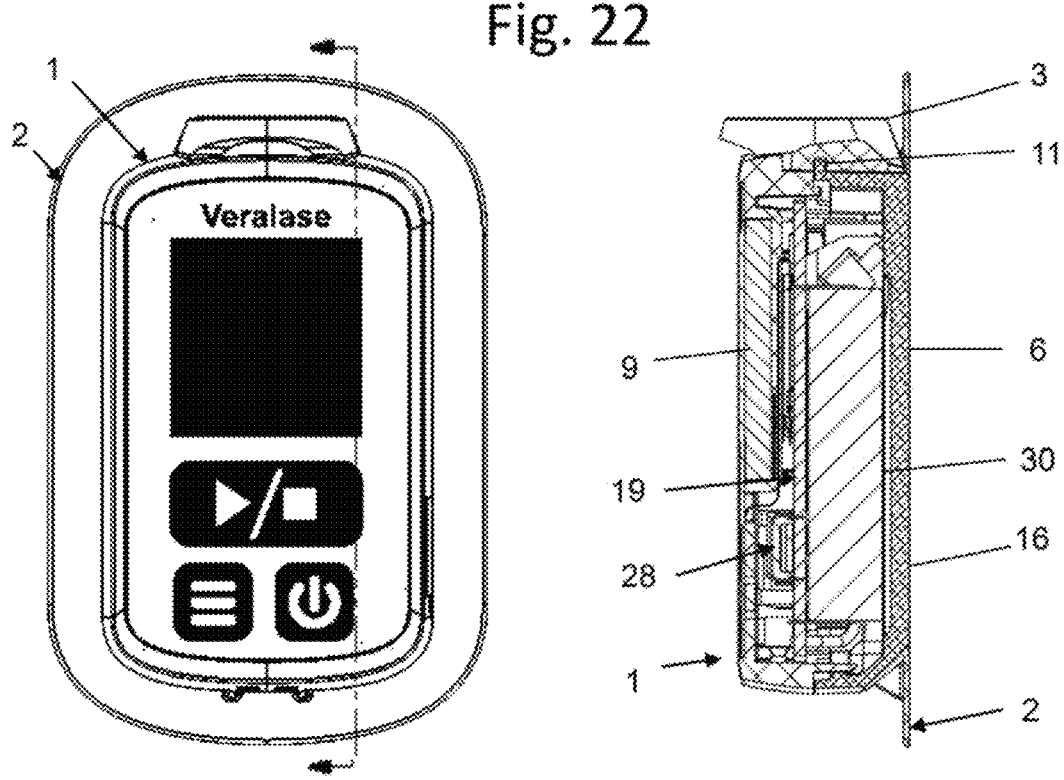
FIG. 22 is a cross-section of FIG. 4 where the cross section plane is directly through the hook 5 and hook feature 13.

Snap feature 11 mates with snap ring 3 preferably to hold the laser system 1 to mounting frame 2 without the need for straps or human holding. For example, snap feature 11 shown in FIG. 8 may be a male tab or the like that interfaces with a receiving region of the snap ring 3 so that these elements snap together and hold until a person applies significant force to intentionally un-snap the connection to separate the snap feature 11 and snap ring 3. FIG. 21 shows how snap feature 11 fits snugly into a pocket in snap ring 3 via this cross-section view.

Figure 7:
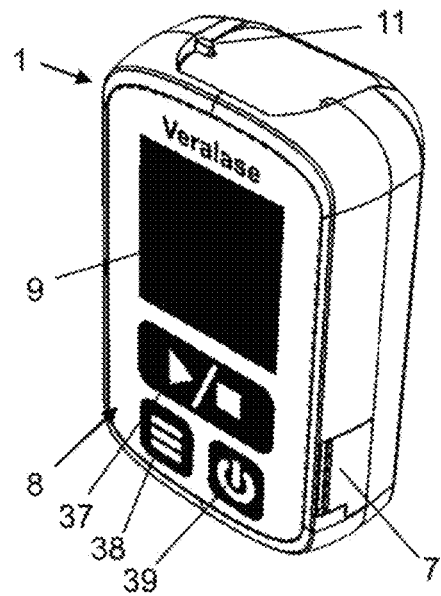
FIG. 7 is a front perspective view of the laser system of FIG. 6.

FIG. 7 is a front perspective of laser system 1 with further detail showing a power button 39, menu button 38 and start/stop button 37, but not limited thereto.

Figure 8:
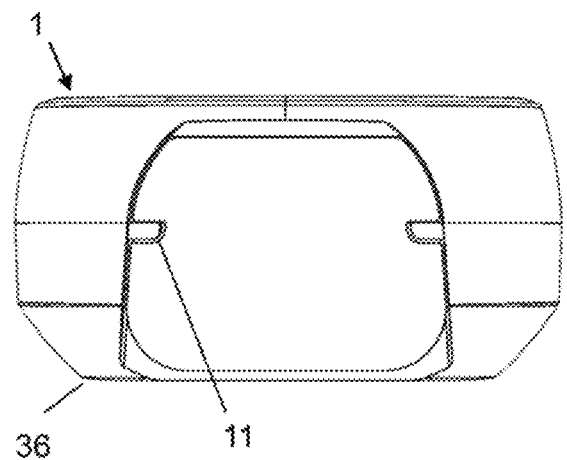
FIG. 8 is a top perspective view of the laser system of FIGS. 6 and 7.

FIG. 8 is a close-up top view of the laser system 1 showing details of the snap feature 11 and laser back edge 36, in accordance with some embodiments. A cavity between the two snap feature tabs 11 seats the snap ring 3 in a flush manner. This hides the snap ring edges when laser is mounted to the person and this approach looks good and is "clean" looking.

Figure 9:
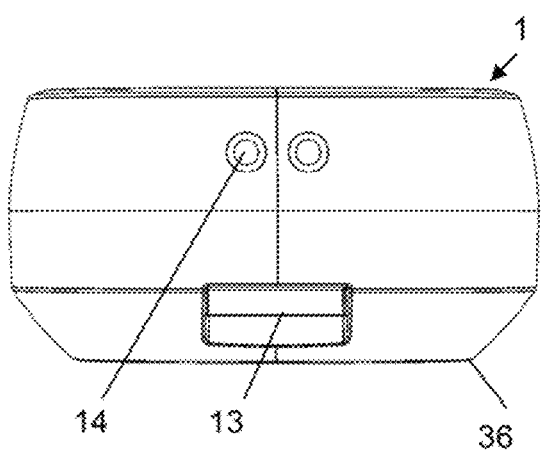
FIG. 9 is a bottom perspective view of the laser system of FIGS. 6-8.

FIG. 9 a close-up bottom-view of the laser system 1. Here, the bottom region of the laser system 1 includes electrical power elements 14, hook feature 13 and laser back edge 36. Hook feature 13 is designed to mate with clip element 5 for mounting the laser system 1 to the mounting frame 2. FIG. 21 shows a cross-section view how hook feature 13 engages with clip element 5. The back edge 36 may include a bevel or the like that extends from the top to bottom of the laser system 1 and further extends from the back surface which directly contacts human skin to a side surface of the laser system 1, for example, shown in FIG. 6. A taper extending from back edge 36 may be used for the laser, which requires extra width to fit all the internal functional components. Also, a relatively narrower contact surface with the skin may be beneficial so it may fit on a young child. Thus, the taper allows for both a smaller contact surface and more internal room for components of the laser.

Figure 10:
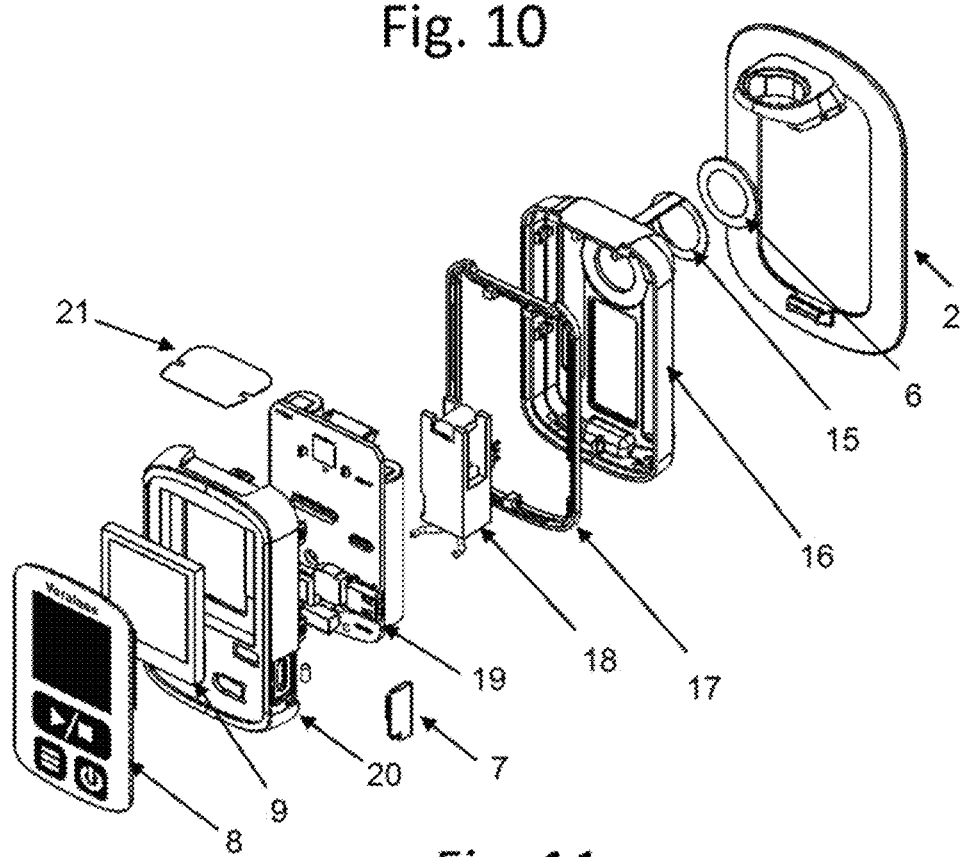
FIG. 10 is an exploded view of the parts of laser system in FIGS. 4-5.

FIG. 10 is an exploded view of laser system 1 showing mounting frame 2, laser transmission window 6, safety sensor 15, laser back 16, seal gasket 17, laser engine 18, port cover 7, control board 19, laser front 20, display 9, membrane touchpad 8, and label 21 of FIGS. 1-9.

The safety sensor 15, which may be configured as a ring-shaped sensor or sensor ring, is mounted behind the laser transmission window 6 and is preferably an integrated ribbon cable of wires that has one or more exposure pads that form behind the laser transmission window 6 and serve as capacitive or resistive sensor elements. The other end of the ribbon plugs into a control board 19 that communicates with, and controls and operates, elements of the laser system 1, such as the display 9, buttons 37-39, and so on. The seal gasket 17 is typically made of a rubber material and seals laser back 16 to laser front 20. As shown in FIG. 10, the laser back 16 and laser front 20 may be standalone components. Port cover 7 seals the side port of laser front 20. Membrane touchpad 8 seals the front of laser front 20. Laser transmission window 6 seals the bottom of laser back 16. Thus, a combination of the foregoing sealing elements permits the contents of the laser system 1 to be completely housed and enclosed. Also, these seals collectively prevent particles, dust, liquids, or other undesirable matter from entering the laser system 1 and causing any damage to the internal parts. These seals are preferentially designed to be water-tight and thereby make the laser system 1 water-proof. The port cover 7 preferably flaps open and closed and is attached to laser front 20 in a hinged manner. Port cover 7 plugs into a USB port or other I/O device on the control board 19 and seals the electronics and laser front from water and particle egress.

Figure 11:
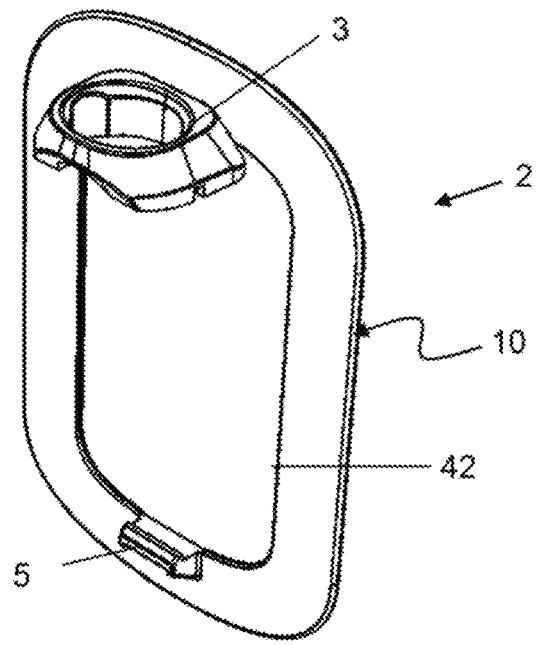
FIG. 11 is perspective view of a mounting frame with shot guide in an up position, in accordance with some embodiments.

FIG. 11 illustrates a mounting frame 2 which is preferably made in one piece of plastic or similar low-cost material. FIG. 11 shows snap ring 3 in an up position as it would be held for the user to mount the laser system 1. Mount frame back region 10 is preferably coated with an adhesive or related bonding material and covered with a wax-like paper prior to use. Mounting frame 2 has an internal edge 42 constructed and arranged to mate precisely with its back edge 36 (see FIG. 6). Clip element 5 is constructed and arranged to mate precisely with hook feature 13 (see FIG. 9).

Figure 12:
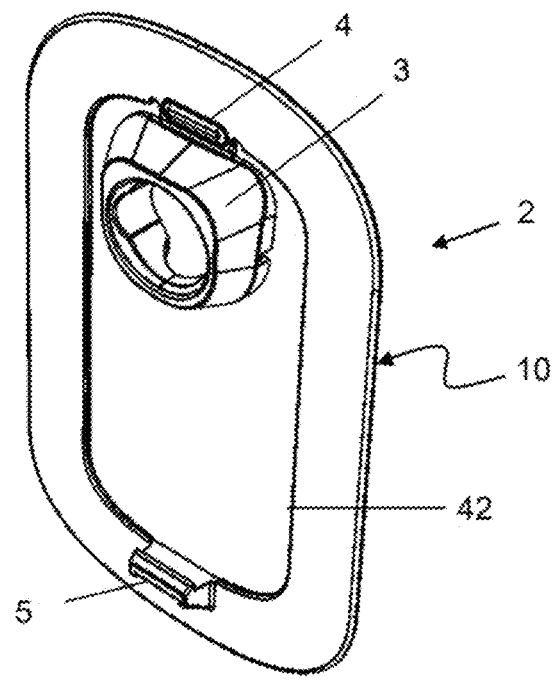
FIG. 12 is perspective view of the mounting frame with shot guide of FIG. 11 in a down position, in accordance with some embodiments.
Figure 23:
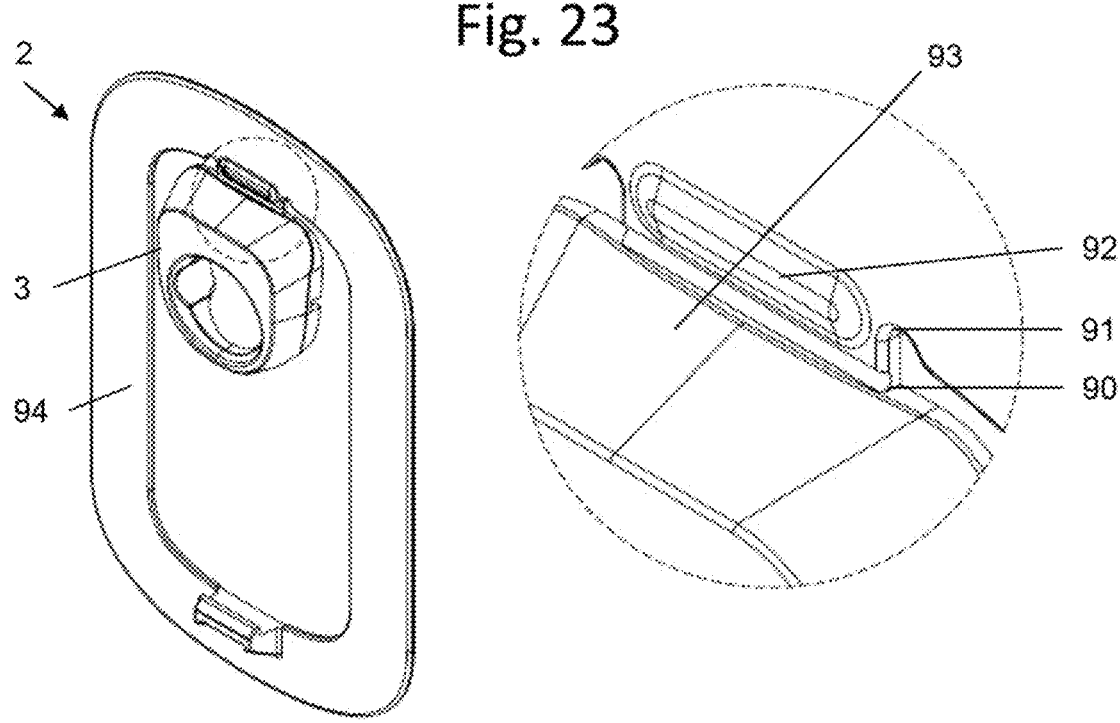
FIG. 23 is a detailed view of the mounting frame of FIG. 12, including a detail view of the hinge area with the snap ring in the relaxed or down position, in some embodiments.
Figure 24:
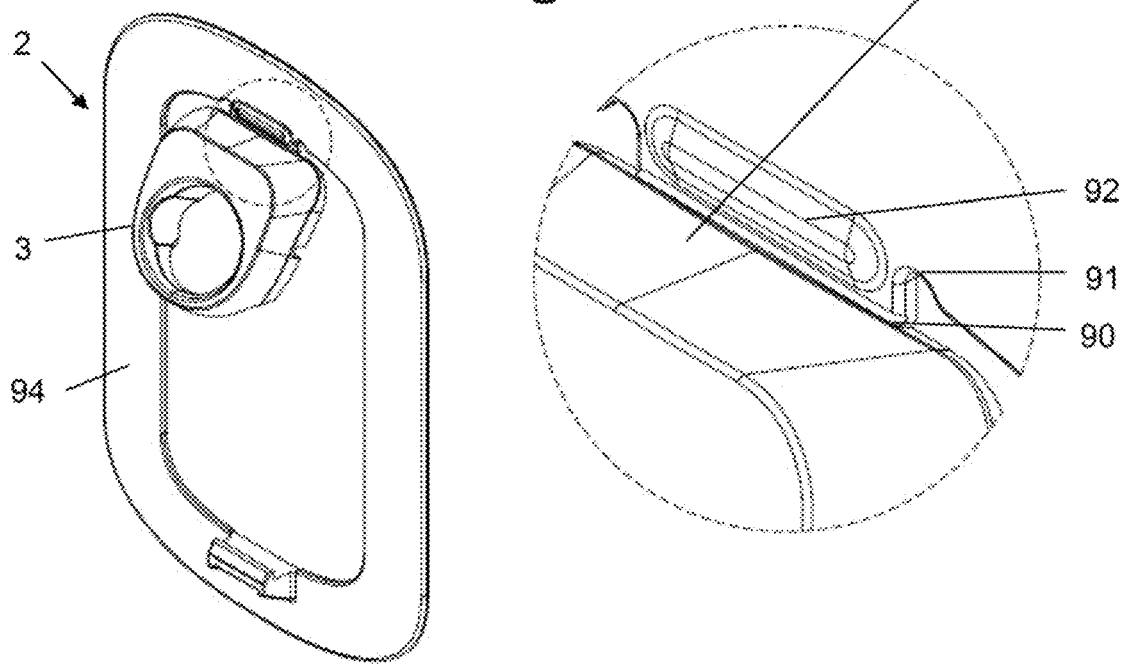
FIG. 24 is a detailed view of the mounting frame of FIGS. 12 and 23, including a detail view of the hinged area with the snap ring in the half-way hinged up position.
Figure 25:
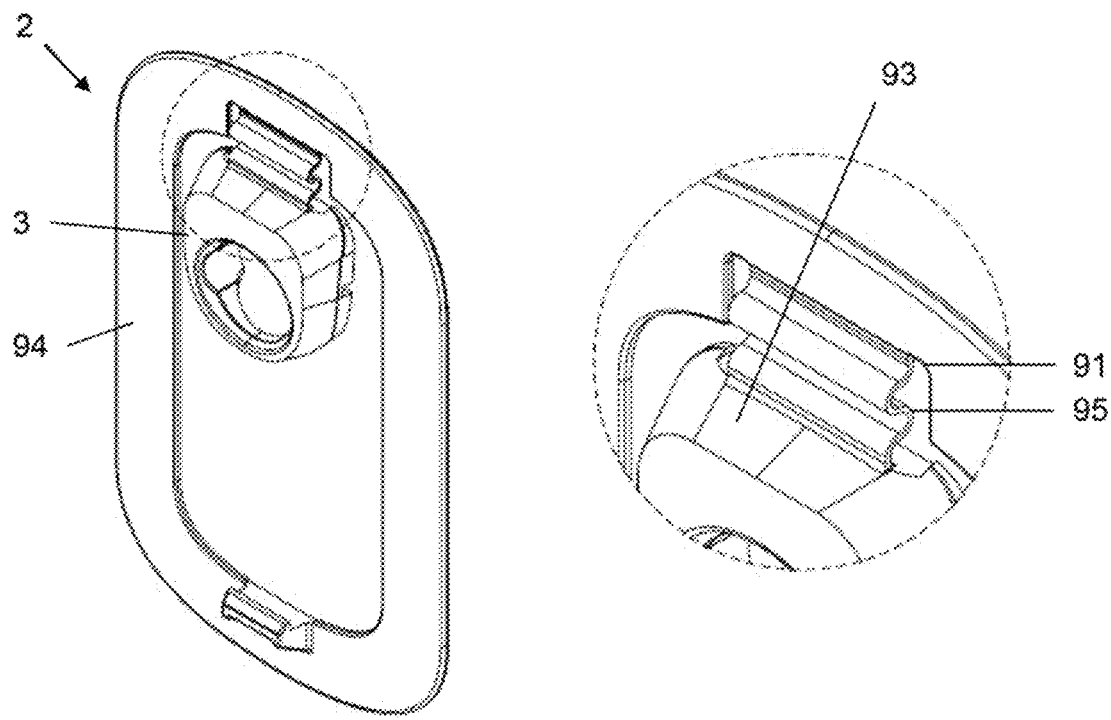
FIG. 25 is a detailed view of the mounting frame of FIG. 12 with a different embodiment of the spring element, including a detail view of the hinge area with the snap ring in the relaxed or down position.
Figure 26:
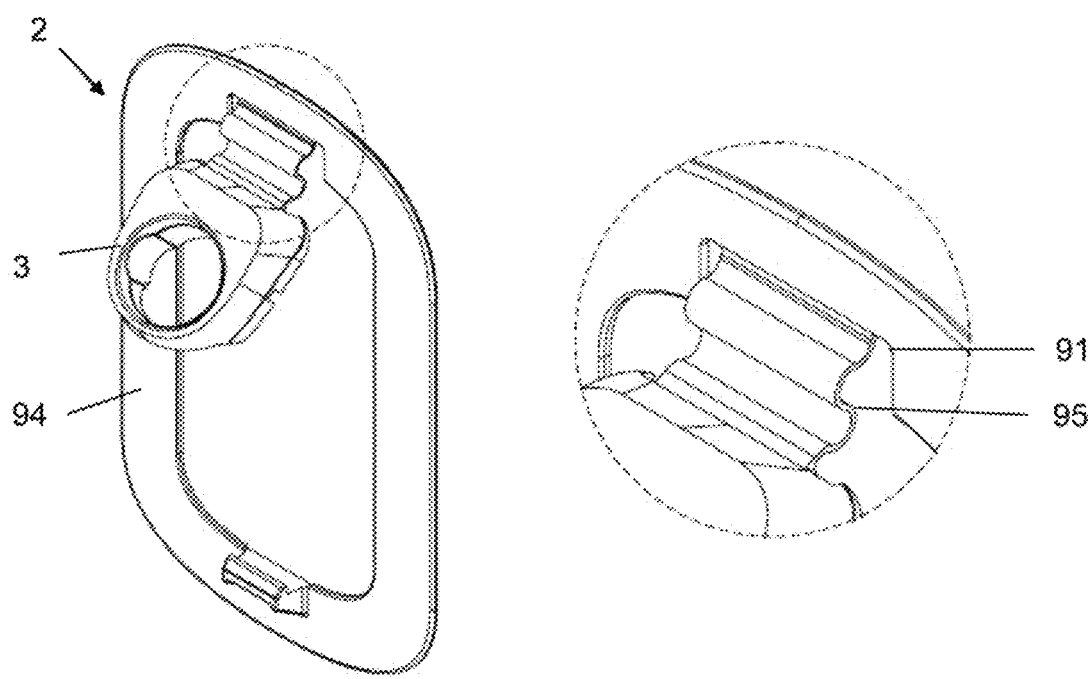
FIG. 26 is a detailed view of the mounting frame of FIGS. 12 and 25 with a different embodiment of the spring element, including a detail view of the hinged area with the snap ring in the half-way hinged up position.

FIG. 12 shows the same mounting frame 2 as in FIG. 11 but shows the snap ring 3 in a down position, which is the position that indicates where the laser treatment will occur or has occurred if treatment has already taken place. FIG. 23 shows an exploded view of the hinge portion of the snap ring. In this exploded view, bend area 90 is thinner than the general thickness of the out rim material 94. This bend area 90 is made of a material with good spring memory such that is will not deform plastically, but will store any bending force applied to it and, when released, the stored force in the material will spring the member back to it fully resting position as shown in FIG. 23. Groove 91 is configured to ensure the bending occurs in bend area 90 and not in other areas. Spring stop 92 is a raised plastic material that will prevent the snap ring back surface 93 from over-extending beyond 90 degrees and damaging the spring force in that material of 90. FIG. 24 shows the snap ring half-way extended; here you can see how the hinge bend occurs at 90 and will stop when surface 93 hits 92. FIG. 25 it identical to FIG. 23 except with a different embodiment of the hinge portion of the snap ring. In this figure, the hinge-spring 95 is made up of two sinusoidal wave-like elements in the area that bends and retains the spring force. This type of hinge-spring causes lower strain or deformation per unit area within plastic material which allows it to avoid plastic deformation and spring back fully when released. Other embodiments of this hinge-spring can have one sinusoidal wave-like element or more than two. FIG. 26 shows snap ring 3 rotated upwards 45 degrees showing how the hinge-spring 95 deforms across a much larger area than the bend area 90 design of FIG. 24.

Figure 13:
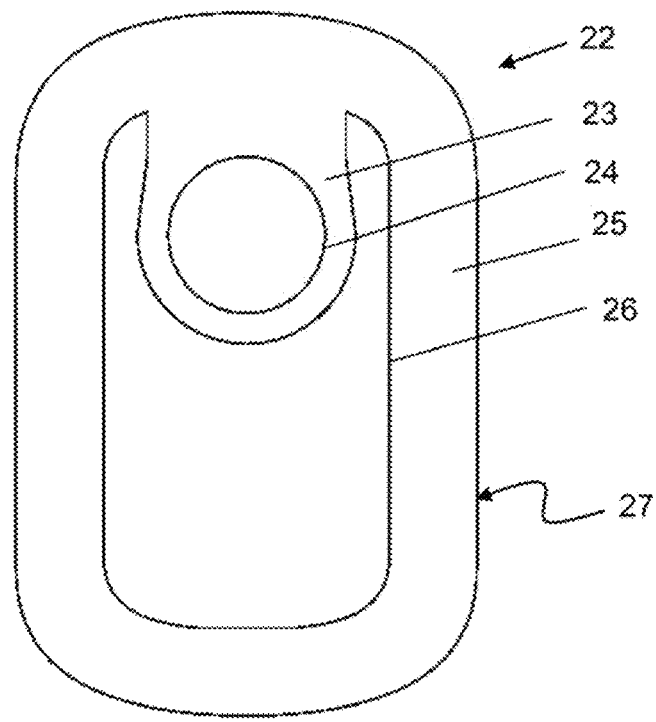
FIG. 13 is perspective view of a sticker used for aligning a laser system and needle, in accordance with some embodiments.

FIG. 13 is a sticker 22 used as an alternate method (in lieu of a mounting frame 2) to align the laser system 1. The sticker 22 has a laser treatment ring edge 24, sticker ring 23, sticker width 25, sticker laser system guide edge 26 and sticker backing 27. The laser treatment ring edge 24 is at least as large as the laser emissions from the laser system 1 and has the same center point when laser back edge 36 is aligned to sticker laser system guide edge 26. This alignment allows the sticker 22 to accurately register the spot being treated by the laser system. The sticker ring is preferably integrated as one piece with the entire sticker 22. The sticker backing 27 is preferably coated with an adhesive or related bonding material and covered with a wax-like paper prior to use. The sticker width 25 is preferably between 5 and 30 mm and relatively uniform around the laser system guide edge 26 geometry. The sticker 22 is preferably formed of a relatively thin piece of paper, vinyl or similar pliable material with adhesive on one side and made at low cost and meant to be disposable.

Figure 14:
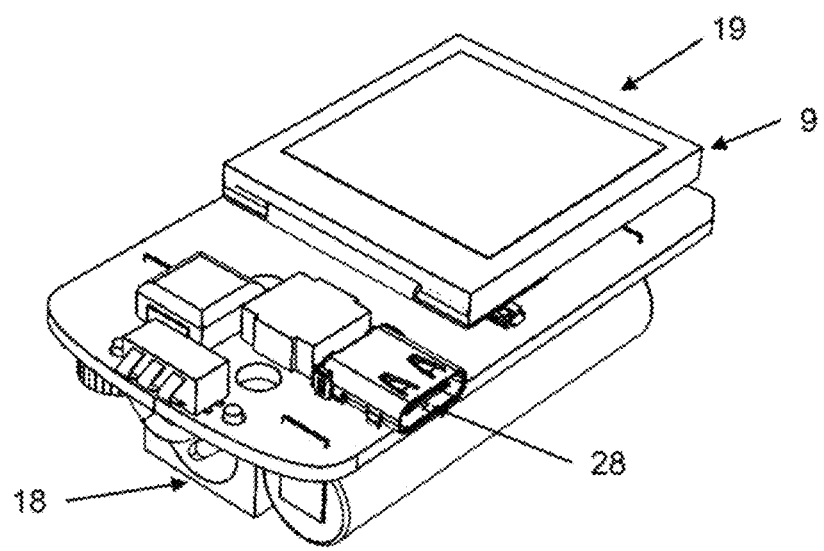
FIG. 14 is a top-side perspective view of a control board of FIG. 10.

FIG. 14 is a control board 19 with display 9 shown mounted on top and laser engine 18 shown underneath, but not necessarily mounted to or touching the control board. USB port 28 is integrated and soldered onto control board 19 such that the port aligns with plastic opening for USB port when assembled. The control board 19 may be implemented as shown in FIG. 10.

Figure 15:
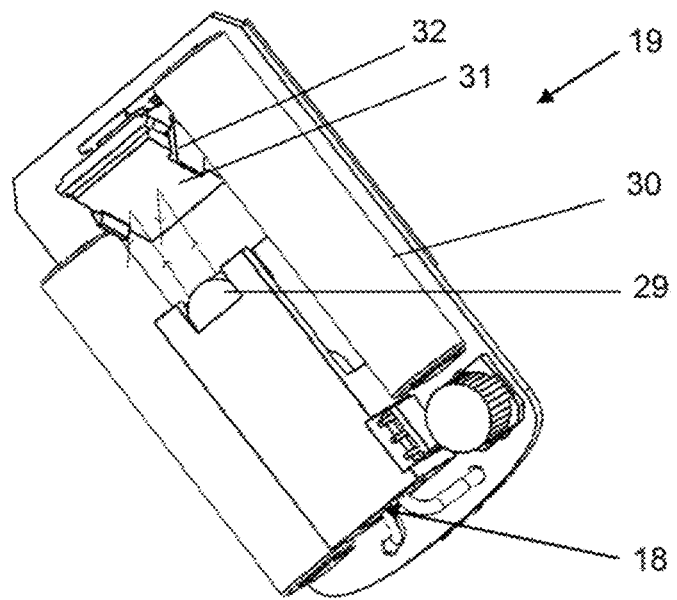
FIG. 15 is a bottom-side perspective view of the control board of FIGS. 10 and 14.

FIG. 15 shows bottom view of the control board 19 in FIG. 14 with laser engine 18 and laser engine lens 29 showing arrows tracing where laser light emits and travels a distance and bounces off mirror 31 held in place by mirror holder 32 which is mounted to control board 19 but may alternatively be mounted to laser back 16. Laser light is preferably generated from laser diodes in the range of 220 nm to 2000 nm. For vaccine adjuvant applications, wavelengths between 1000 to 1310 nm are preferred with most-preferable wavelengths between 1250 and 1290 nm. At least one battery 30 is attached to control board 19 for providing power to electronic components such as display 9. In some embodiments, two batteries 30 may be positioned in the control board 19, as shown, but not limited thereto.

Figure 16:
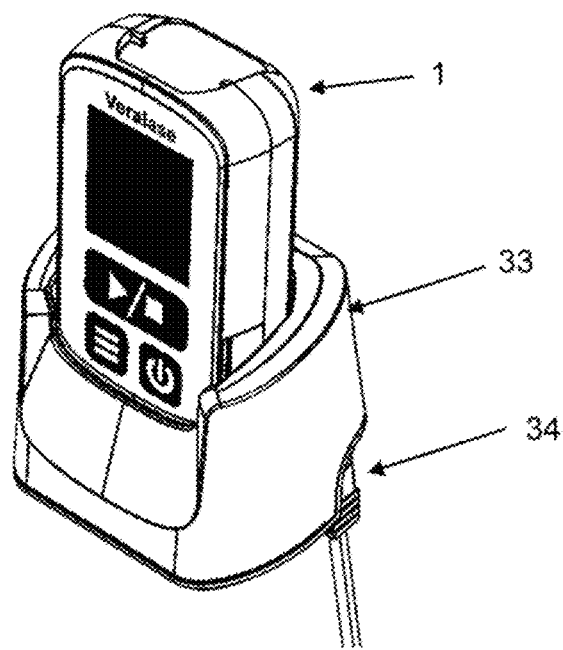
FIG. 16 is a front-side perspective view of the laser system of FIG. 6 in a docking station, in accordance with some embodiments.

FIG. 16 shows laser system 1 mounted in docking station 33 with attached power cord 34. Docking station 33 includes a cradle constructed for receiving and holding in place the laser system 1 and for charging the battery(s) 30 via electrical contacts 43 (see FIG. 18) that directly abut the electrical power elements 14 at the bottom of the laser system 1, for example, shown in FIG. 9.

Figure 17:
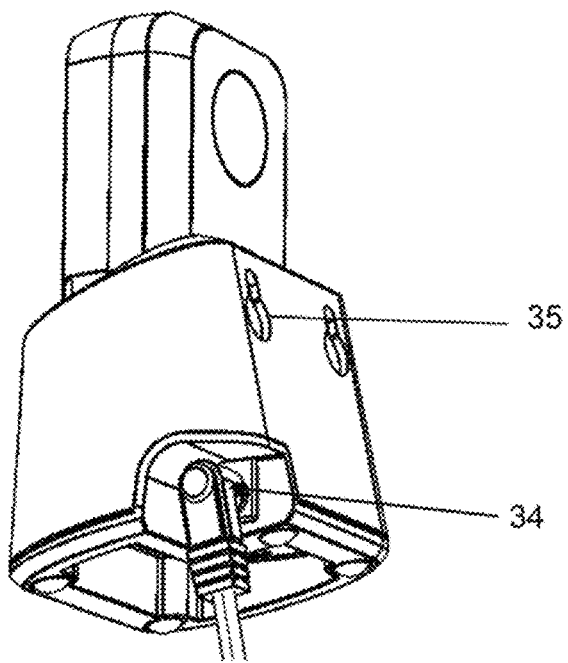
FIG. 17 is a back-side perspective view of the laser system of FIGS. 6 and 16 in the docking station.

FIG. 17 shows a backside view of system in FIG. 16 with docking station mounting holes 35 and power cord 34. The mounting holes 35 are for inserting into screws or other male elements extending from a wall or other side surface for hanging the docking station 33 or the like. The power cord 34 extends between a power source such as an electrical outlet and the electrical contacts 43 in the cradle which provides power to the laser system battery(s) 30 when the electrical contacts 43 directly abut the electrical power elements 14 at the bottom of the laser system 1.

Figure 18:
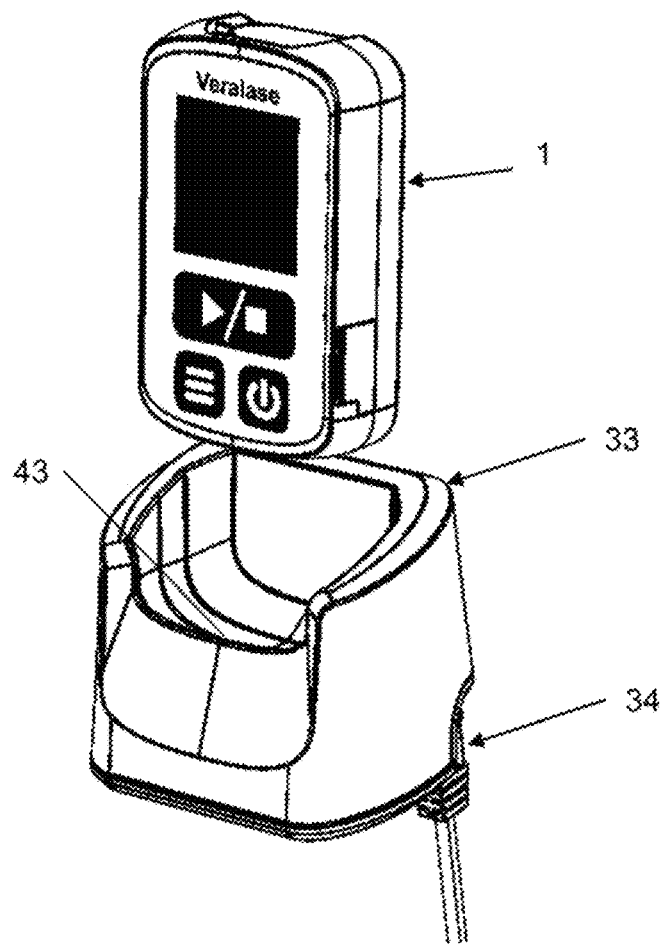
FIG. 18 is the system and docking station of FIGS. 16 and 17 with a laser system not yet docked.

FIG. 18 shows laser system 1 just before docking with docking station 33. Electrical contacts 43 are in the bottom of the docking station 33 and mate with electrical power elements 14 of laser system 1 and provide electrical charging of battery in the laser system control board 19.

Figure 19:
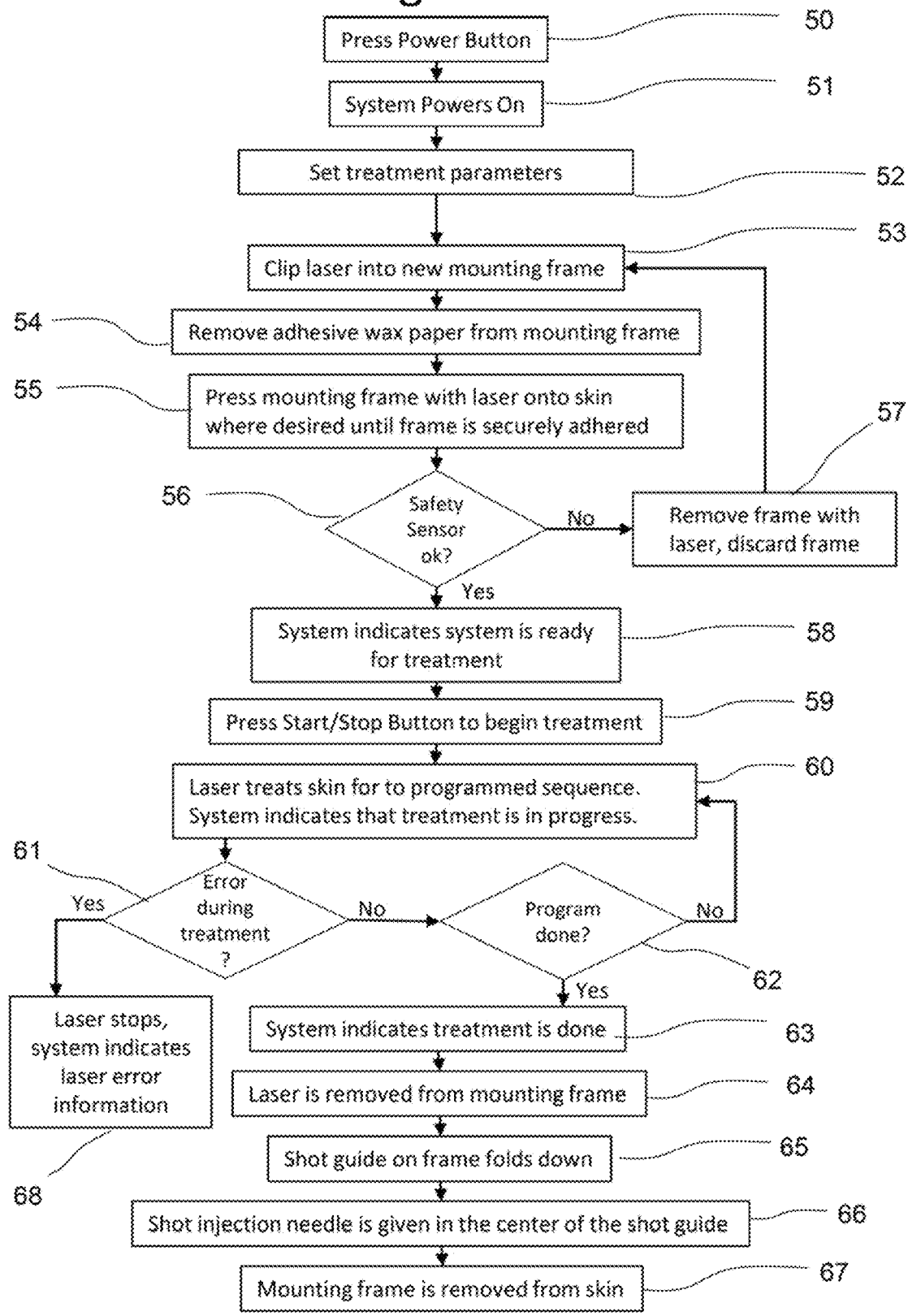
FIG. 19 is a flow chart of a method of operation of the laser system, in accordance with some embodiments.

FIG. 19 is a flow chart of a method for administering laser treatments using a mounting frame 2, in accordance with some embodiments. In describing the method of FIG. 19, reference is made to elements of FIGS. 1-18.

In more detail, the power button 39, e.g., FIG. 7, is pressed to energize the laser system 1 in step 50. Once the power button 39 is engaged, the system 1 includes a special-purpose hardware processor for launching into step 51. Here, an audio signal may be generated such as a jingle from a speaker or buzzer element on the control board 19. Then, the indicator lighting of display 9 lights up to indicate that the system power is on and indicate which preset laser program/power level the device is set to perform at.

Upon initial power up in step 51, the default power level is automatically set for the user by the system control program. In step 52, the user may now press the power button 39 again as a power/program select button to change the power/program that will be used once the laser is in operation. The user may continue to press the power button 39 to cycle through power levels such as low to medium to high, back to low, and so forth. Each time the power button 39 is pressed, the LED lights or display 9 may change laser setup configurations to represent the power level selection or setup for a given treatment. For example, pressing the power button may be configured to adjust the laser power level for a given treatment. The doctor or medical professional may select the appropriate power level based on the age, gender, and treatment purpose. Another use of the power select button is to cycle through laser configurations for specific indications. For example, the initial power level may be defined as "Vaccine adjuvant" and when the button is pressed a second time, the next program indication is shown as "foot fungus", and after another press, the display indicates a third treatment configuration such as "Acne treatment", and so on. In this way, one laser device may be configured at the factory for several treatment indications and the doctor may cycle to the appropriate treatment indication laser configuration by pressing the power button until the desired indication is displayed. This is beneficial, convenient and cost-effective to the doctor as one device may be used for several medical procedures.

The user may apply a mounting frame 2 in step 53 by pulling up the snap ring 3, for example, in the up position shown in FIG. 11, and inserting the laser system 1 into the mounting frame 2 making sure that the hook feature 13 mates snugly with clip element 5 prior to depressing the snap ring 3, then securely latching it onto snap feature 11 which locks the laser system 1 onto the mounting frame 2, for example, illustrated at FIGS. 4 and 5.

In step 54, the use removes the adhesive cover paper from the mounting frame back region 10 to expose the adhesive surface of the mounting frame back region 10.

In step 55, the user may position the combined laser system 1 mounted in mounting frame 2 against the human skin at a region of interest on the skin, by pressing the adhesive surface firmly against the skin until the system 1 is securely adhered to the human skin.

Once the laser back 12 and laser transmission window 6 are in good contact with the skin, the safety sensor ring 15 will provide an electrical signal to the control board 19 and the laser system 1 will indicate the system is ready for treatment via sounds and/or changes to display 9. The electrical signal from safety sensor 15 is typically a measurement of capacitance or resistance. These measurement change based on the proximity of human skin or tissue to the sensor. The sensor and control board are calibrated to measure when human skin or tissue is less than 2 mm from touching the laser back 12 or laser window 6 and preferably in direct contact with both laser back and window. The laser system 1 continually checks to see if the safety sensor ring 15 is in good contact/proximity with the skin. In step 56, if skin contact or predetermined proximity from the skin is not sufficient, then the method proceeds to step 57, where the display 9 presents information for a viewer or listener with updates including information to discard the mounting frame 2 and with further instructions, for example, to clip the laser system 1 to a different mounting frame, for example, described in step 53. If at decision diamond 56 a determination is made that it is acceptable to proceed with a treatment, then the method may proceed to step 58 where the system indicates it is ready for treatment to commence, which is typically done through sounds and updates to the display 9. A special purpose processor of the system 1 may execute program instructions to perform one or more of the method steps, for example, decision diamond 56.

At step 59, to begin treatment, the medical professional presses the start/stop button 37. This causes the laser system 1 to begin its programmed sequence of laser treatment in step 60, which is directed through the laser transmission window 6 at the region of interest of the skin. At step 60, the laser system 1 treats the skin according the programmed sequence. In doing so, the system 1 may display information, for example, at the display 9 or illuminating a display LED or the like including an indicator that the treatment is in progress. Also, in doing so, the system 1 continually checks for errors. Accordingly, at decision diamond 61, if an error is encountered during treatment, then the laser system stops in step 68, an alarm or other sound may be generated from the system 1, and/or the display 9 may be updated to display error information and next steps for the user. For example, if the laser system 1 is removed from skin during laser treatment, safety sensors and the control board will determine this error and immediately stop the laser from firing, then display the error code such as "Error 6: Laser lost contact with skin. Please remove system and start again." At decision diamond 61, if no errors are encountered, then the system 1 simultaneously checks if the program is completed. At decision diamond 62, a determination is made in response to a determination of no errors whether the programmed sequence is complete. If yes, then the system 1 transitions to step 63 whereby the display 9 is updated and an audio and/or visual indicator is generated to indicate to the user that the treatment is completed.

At step 64, the laser system 1 is removed from the mounting frame 2 and the snap ring 3, also referred to herein as a shot guide, of the mounting frame 2 is folded down onto the skin in step 65 to outline the laser treatment area and guide any medical shot/vaccination as needed. Preferably, the snap ring 3 in step 65 springs down automatically when laser system 1 is removed. The hinge 4 between snap ring and flat part of mounting frame incorporates a plastic spring which is compressed when the snap ring is retracted upwards and the spring pressure is release when the snap ring is rotated downward where it would be approximately flush against skin when mounted. The spring is preferably similar to a leaf-spring mechanism which holds energy when compressed and releases this energy when the holding force is removed. As needed, step 66 occurs with a medical person administering a shot using the snap ring 3 as a guide to center the shot to the laser treatment area. Finally, in step 67, the mounting frame 2 is removed and discarded.

Once the user is completely done using the laser system 1 to treat the skin, the user can allow the system 1 to shut down automatically, as the system is programmed to time-out within a short time of no buttons being pressed, for example, about 2 minutes. Alternatively, the user may hold the power button 39 for more than about 1 second and the laser system 1 will power down due to a signal sent in response to the pressed power button to the system electronics. When the laser system 1 powers down, it may play a lower-tone jingle or other audio output as compared to the start-up tone, and all display elements turn off.

For indications where it is more important to line up the laser treatment with a specific spot on the patient, such as in treating a wart, rash or fungus area, it is preferable to implement steps 54 and 55 first, followed by step 53. This sequence allows the medical professional to ensure that the snap ring 3 (and subsequent laser treatment) is lined up with the area of interest for treatment.

Figure 20:
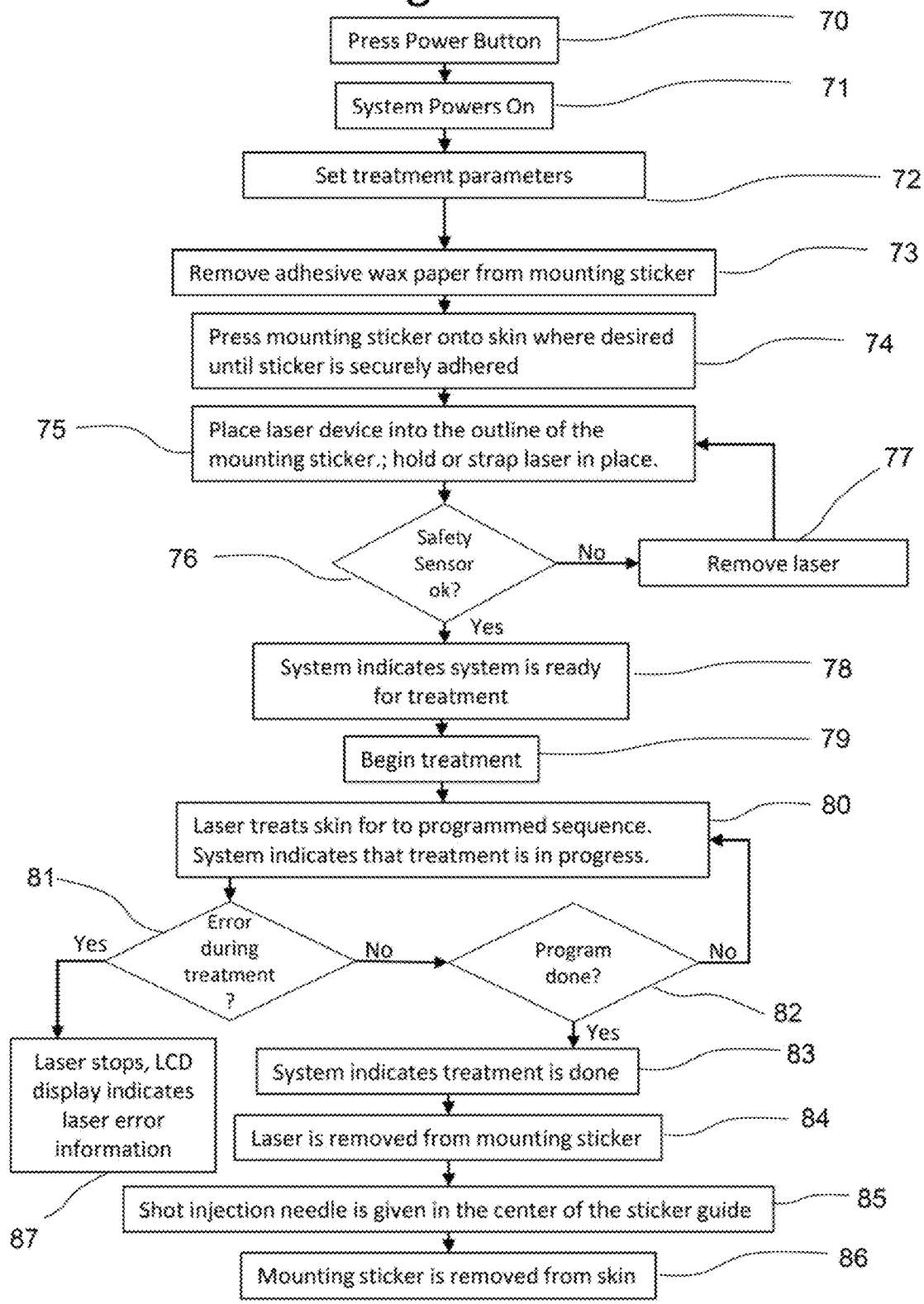
FIG. 20 is a flow chart of an alternate method of operation of the laser system, in accordance with some embodiments.

FIG. 20 is a flow chart outlining an alternate method of implementing the laser treatment by using a sticker 22 instead of a mounting frame. In this process, steps 70-72 operate identically to steps 50-52, so details are not repeated for brevity. At steps 73-74, as sticker is used instead of a mounting frame 2, the sticker is adhered directly to the skin in the desired spot via an adhesive backing. In step 75, the laser system 1 is placed into the outline of the sticker such that the laser back edge 36 align with the sticker laser system guide edge 26 and the laser transmission window 6 aligns with laser treatment ring edge 24. The laser system 1 is manually held in place during the treatment process or preferably strapped into place. Steps 76-83 and 87 correspond exactly to steps 56-63 and 68 and operate identically, so details are not repeated for brevity. In step 84, the laser system 1 is manually removed from the skin, if manually held or unstrapped if strapped in place. Steps 85-86 are performed identically to steps 66-67, so details are not repeated for brevity.

The size of the laser system is preferably no larger than 72×44×23 mm in size in any or all of those dimensions. The width of the mounting frame perimeter is preferably less than 20 mm and typically around 10 mm.

Using the port behind port cover 7, the user can plug in a USB cord or similar to make an electrical and/or programming connection to laser system 1. This connection allows the user to charge the laser system batteries and program the device as needed. Likewise, the system may be equipped with a Bluetooth device or other wireless interface and corresponding program code stored in a computer memory device and executed by a hardware processor, and the user may pair the laser system 1 via Bluetooth connection or the like to an external device capable of programming or communicating with the laser system 1. Applications or apps on cell phones, tablets or PCs can allow for this Bluetooth connection and allow for the user to have a robust interface with laser system to program, track laser usage, and configure the device. This connection can also synchronize data between the device and an external database for the purposes of storing data, updating software and firmware and other programming functions. Such synchronization may occur automatically and could also involve commerce such as managing usage charges and allotted time on the device.

To summarize the preferable operation of the system: Typically, the medical professional will mount the laser system 1 onto the frame 2 and secure by snapping the snap-ring 3 down to mate with the snap feature 11, then peel off a protective paper material off the backside of the frame 2 to expose the back region's 10 adhesive surface of 2, then apply the integrated laser system and frame to the person's skin and adhere the mounting frame 2 and backside of the laser back 12 to the person using the adhesive interface. Once this is done, the buttons on the membrane touchpad 8 or the display 9 to start the laser operation. Once the laser treatment is completed, the medical professional will remove the laser by un-snapping snap ring 3 from laser system 1 and removing the laser system. Once the laser system is removed, the snap ring 3 will automatically rotate towards the skin surface and provide a guide for the medical professional to then administer the shot with a syringe 40 or similar drug delivery device. Once the shot is administered the medical profession or person getting the shot peels off the mount frame to complete the process. As an alternative to a needle shot, user may use a trans-dermal patch to administer the vaccine or medicine after the laser system is removed following the laser irradiation.

It is to be understood that the foregoing description is intended to illustrate and not to limit the scope of the invention, which is defined by the scope of the appended claims. Other embodiments are within the scope of the following claims.

What is claimed is:

1. A system for providing a localized laser treatment to a targeted region of skin or tissue for treating a patient, the system comprising:
 a laser system, comprising:
  a surface; and
  a laser transmission window at the surface from where a source of laser light is output;
 a removable frame or strap, comprising:
  an adhesive backing or locking compressive strapping that attaches to a region surrounding a targeted region of patient skin or tissue; and
  at least one connecting member for removably, securely, and precisely coupling the laser system to the frame or strap so that the surface including the laser transmission window is positioned at an interior region of the frame or strap, and so that the source of laser light is output through the interior region of the frame or strap to form an irradiation spot at the targeted region of skin or tissue, wherein the system further comprises:
  a pivotable registration member that, in a first position, is removably coupled to the surface of the laser system, and in a second position is positioned over the targeted region of skin or tissue and has a common center with the irradiation spot formed at the targeted region of skin or tissue.

2. The system of claim 1, wherein the laser system outputs the source of laser light to form the irradiation spot at the targeted region of skin or tissue between 2 seconds and 60 minutes.

3. The system of claim 1, wherein the laser system includes at least one laser diode that outputs the source of laser light in the range of 220 nm to 2000 nm.

4. The system of claim 1, further comprising a hinge between the pivotable registration member and a flat region of the frame, the hinge including a spring which is in compression when the pivotable registration member retracted upwards and the spring pressure is released when the pivotable registration member is rotated downward where it is adjacent the targeted region of skin or tissue when mounted.

5. The system of claim 1, further comprising a capacitive or resistive safety sensor behind the laser transmission window, for generating an electrical signal when a back surface of the laser system and the laser transmission window are in contact with the targeted region of skin.

6. The system of claim 1, further comprising a wireless interface that establishes an electronic communication between the laser system and an application on a remote mobile device to program, track laser usage, and configure the laser system remotely from the remote mobile device.

7. The system of claim 1, further comprising a docking station for charging the laser system.

8. A system for providing localized laser treatment of a targeted spot of skin or tissue for treating a patient, comprising:
 a laser system including a side surface from which laser light is emitted; and
 a marking or inking system including a stamp, stencil, or writing instrument or removable sticker for marking the targeted spot skin or tissue to form an outline that aligns with or matches an outside edge of the laser system or corresponding marking fiducials, wherein when a laser system light emitting surface is held against the targeted spot of skin or tissue and the laser system outside edge is aligned with the skin or tissue markings, the laser emission area on the skin or tissue has a common center to skin or tissue markings, and the common center provides an accurate indication of where laser light treated the skin or tissue after the laser system is removed.

9. A system for providing a localized laser treatment to a targeted region of skin or tissue for treating a patient, the system comprising:
 a laser system no larger than 120×80×40 mm in any dimension of size;
one surface of the laser where laser light emissions exit the device which is in direct contact with targeted skin or tissue, wherein the laser system produces a peak laser output power capable of 20 mW or greater.

10. The system of claim 9, wherein the laser system has a volume of no more than 384 $cm^3$ or 240 $cm^3$.

11. The system of claim 9, wherein the laser system outputs a source of laser light having a wavelength between 200 and 2000 nm.

12. The system of claim 9, wherein the laser system outputs a source of laser light having a wavelength between 1000 and 1400 nm.

13. The system of claim 9, wherein the laser system outputs a source of laser light having a wavelength between 1200 and 1310 nm.

14. The system of claim 9, wherein the laser system outputs a source of laser light having a wavelength between 1250 to 1300 nm.

15. The system of claim 9, further comprising:
the laser system is used for the treatment of warts, foot fungus, skin rashes, or wound healing, or as a vaccine adjuvant.

16. The system of claim 9, further comprising:
wherein contact with the human skin or tissue proves thermal heat stabilization between 20 to 40 C.

17. The system of claim 9, further comprising:
a capacitive or resistive safety sensor used to ensure device is engage with the skin or tissue.

18. The system of claim 9, wherein the system is battery-powered and cordless.

19. A system for providing a localized laser treatment to a targeted region of skin or tissue for treating a patient, the system comprising:
a laser system, comprising:
a surface; and
a laser transmission window at the surface from where a source of laser light is output;
a removable frame or strap, comprising:
an adhesive backing or locking compressive strapping that attaches to a region surrounding a targeted region of patient skin or tissue; and
at least one connecting member for removably, securely, and precisely coupling the laser system to the frame or strap so that the surface including the laser transmission window is positioned at an interior region of the frame or strap, and so that the source of laser light is output through the interior region of the frame or strap to form an irradiation spot at the targeted region of skin or tissue, the system further comprising:
a hinge between a pivotable registration member that outlines the targeted region of skin or tissue via the interior region of the frame or strap and the frame, the hinge including a spring which is in compression when the pivotable registration member retracted upwards and the spring pressure is released when the pivotable registration member is rotated downward where it is adjacent the targeted region of skin or tissue when mounted.

* * * * *